United States Patent
Martinetti et al.

(10) Patent No.: US 9,408,798 B2
(45) Date of Patent: *Aug. 9, 2016

(54) DISSOLVABLE FILMS CONTAINING HIGH CONCENTRATIONS OF NONIONIC SURFACTANTS SUCH AS POLYSORBATES TO ENHANCE HIGH SOLID LOADINGS

(75) Inventors: Melissa Martinetti, Bridgewater, NJ (US); Rajan Jabbal, Old Bridge, NJ (US)

(73) Assignee: Colgate-Palmolive Company, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 13/513,617

(22) PCT Filed: Dec. 4, 2009

(86) PCT No.: PCT/US2009/066727
§ 371 (c)(1),
(2), (4) Date: Jun. 4, 2012

(87) PCT Pub. No.: WO2011/068513
PCT Pub. Date: Jun. 9, 2011

(65) Prior Publication Data
US 2012/0244090 A1    Sep. 27, 2012

(51) Int. Cl.
| | | |
|---|---|---|
| *A61Q 11/00* | (2006.01) | |
| *A61K 8/84* | (2006.01) | |
| *A61K 8/86* | (2006.01) | |
| *A61K 8/02* | (2006.01) | |
| *A61Q 5/00* | (2006.01) | |
| *A61Q 19/00* | (2006.01) | |

(52) U.S. Cl.
CPC ... *A61K 8/86* (2013.01); *A61K 8/02* (2013.01); *A61K 8/0216* (2013.01); *A61Q 11/00* (2013.01); *A61Q 5/00* (2013.01); *A61Q 19/00* (2013.01)

(58) Field of Classification Search
USPC .................................................. 424/49, 401
See application file for complete search history.

(56) References Cited

U.S. PATENT DOCUMENTS

| | | |
|---|---|---|
| 4,022,880 A | 5/1977 | Vinson et al. |
| 4,820,506 A | 4/1989 | Kleinberg et al. |
| 4,839,157 A | 6/1989 | Mei-King Ng et al. |
| 4,900,552 A | 2/1990 | Sanvordeker et al. |
| 5,047,244 A | 9/1991 | Sanvordeker et al. |
| 5,695,746 A | 12/1997 | Garlick, Jr. et al. |
| 5,700,478 A | 12/1997 | Biegajski et al. |
| 5,948,430 A | 9/1999 | Zerbe et al. |
| 6,231,957 B1 | 5/2001 | Zerbe et al. |
| 6,241,974 B1 | 6/2001 | White, Jr. et al. |
| 6,315,986 B1 | 11/2001 | Wong et al. |
| 6,596,298 B2 | 7/2003 | Leung et al. |
| 6,669,929 B1 | 12/2003 | Boyd et al. |
| 2003/0053962 A1 | 3/2003 | Zerbe et al. |
| 2004/0115137 A1* | 6/2004 | Verrall et al. ................... 424/48 |
| 2005/0019273 A1 | 1/2005 | Boyd et al. |
| 2005/0106112 A1 | 5/2005 | Boyd et al. |
| 2007/0020201 A1 | 1/2007 | Boyd et al. |
| 2007/0140985 A1 | 6/2007 | Boyd et al. |
| 2007/0218114 A1 | 9/2007 | Duggan et al. |
| 2007/0231441 A1 | 10/2007 | Verrall et al. |
| 2008/0160056 A1 | 7/2008 | Boyd et al. |

FOREIGN PATENT DOCUMENTS

| | | |
|---|---|---|
| CN | 1812762 | 8/2006 |
| CN | 1913862 | 2/2007 |
| CN | 1925835 | 3/2007 |
| RU | 2006125452 | 1/2008 |
| WO | WO 00/56276 | 9/2000 |

OTHER PUBLICATIONS

ISR and Written Opinion for PCT/US2009/066727 mailed Oct. 4, 2010.
Written Opinion for PCT/US2009/066727 mailed Feb. 22, 2012.

* cited by examiner

*Primary Examiner* — Lezah Roberts

(57) ABSTRACT

An oral care composition and method are described in which the composition includes a film or a plurality of film fragments entrained in a carrier. The film or plurality of film fragments comprises a relatively high concentration of nonionic surfactants. The composition and methods provide benefits including higher active material loading in the film formula for improved efficacy, and a reduced amount of film needed in a product, which at the same time delivering comparable or improved efficacy with lower loading of the film in the composition.

18 Claims, No Drawings

DISSOLVABLE FILMS CONTAINING HIGH CONCENTRATIONS OF NONIONIC SURFACTANTS SUCH AS POLYSORBATES TO ENHANCE HIGH SOLID LOADINGS

CROSS-REFERENCE TO RELATED APPLICATION

This application is a national stage entry under 35 U.S.C. §371 of International Patent Application No. PCT/US2009/066727, filed 4 Dec. 2009, which is incorporated herein by reference.

BACKGROUND

This application relates to oral and personal care compositions, and more particularly to compositions comprising a film entrained in a carrier, in which the film includes a relatively high concentration of nonionic surfactants such as polysorbates. Such compositions include, for example, dentifrices. The high concentration of nonionic surfactants enhance the solid loading capacity of the film.

The aesthetic appeal of such compositions is important, and can have significant effects on consumer acceptance and usage. Aesthetic effects have been acknowledged to play an important role in consumer acceptance of many products. Although such products have met with consumer approval, the art seeks to further improve the aesthetic effects as well as the cosmetic and therapeutic benefits of these products. Indeed, many such compositions known in the art are deficient in one or more attributes.

Compositions for enhancing health, hygiene or appearance, such as oral care compositions, skin care compositions and hair care compositions, are used by millions of people. These compositions are used for a wide variety of purposes, including for enhancing personal health, hygiene, and appearance, as well as for preventing or treating a variety of diseases and other conditions in humans and in animals.

The formulation of such compositions presents a number of challenges. They must be pharmaceutically and/or cosmetically acceptable for their intended use. Compositions that contain therapeutic active materials preferably deliver the active at effective levels, avoiding undue chemical degradation. Similarly, compositions containing cosmetically functional materials must deliver the material to, e.g., the oral cavity, skin or hair at effective levels under the conditions that they are typically used by the consumer.

Water-soluble films for oral administration of therapeutic agents are well known in the art. It is also known in the art to use such films for administering a breath freshening agent, e.g., menthol. The known films for administering breath freshening agents and/or active pharmaceutical agents are generally comprised of at least one water-soluble polymer suitable for human consumption and at least one compound that enhances the wettability of the water-soluble polymer, typically selected from polyalcohols, surfactants and plasticizers. For example, U.S. Pat. No. 5,948,430, the disclosure of which is incorporated by reference herein in its entirety, describes a monolayer film that can be adhered to the oral cavity to release a pharmaceutically or cosmetically active ingredient, wherein the film comprises at least one water-soluble polymer; at least one member selected from the group consisting of a polyalcohol, a surfactant and a plasticizer; at least one cosmetic or pharmaceutically active ingredient; and a flavoring agent.

U.S. Pat. No. 5,700,478, the disclosure of which is incorporated by reference herein in its entirety, describes a laminated device for controlled release of a substance within a mucosa-lined body cavity including a water-soluble adhesive layer comprised of a water-soluble polymer and a water-soluble plasticizer, and a water-soluble polymer layer. This patent teaches a multiple layer laminate that dissolves relatively slowly for controlled or sustained release of a substance.

U.S. Pat. No. 4,900,552, the disclosure of which is incorporated by reference herein in its entirety, describes a trilaminate film suitable for prolonged and sustained delivery of an active ingredient in a buccal cavity. The trilaminate includes a hydratable muco-adhesive base layer; a non-adhesive reservoir layer; and a water-impermeable barrier sandwiched between and bonded to the base layer and the reservoir layer. This patent discloses slowly disintegrating films for prolonged or sustained release of a substance.

U.S. Pat. No. 5,047,244, the disclosure of which is incorporated by reference herein in its entirety, discloses a therapeutic dosage form comprising an anhydrous but hydratable monolithic polymer matrix that contains amorphous fumed silica as well as a therapeutic agent, and a water-insoluble barrier layer secured to the polymer matrix and defining a non-adhesive face. This patent does not disclose rapidly disintegrating films, but instead contemplates compositions that are capable of providing improved availability of therapeutic agents from a controlled release muco-adhesive carrier system.

U.S. Pat. No. 6,669,929, and U.S. Patent Application Publication No. 2003/0053962, the disclosures of each of which are incorporated by reference herein in their entirety, disclose film forming agents useful in oral care compositions. The films dissolve in the mouth and release functional components, typically flavorants.

It is known to incorporate flavorants, colorants, and some active components in films that dissolve in the oral cavity. These films are used either by themselves as breath freshening strips, teeth whitening strips, or as polymer flakes dispersed throughout an oral care composition. It also is known to incorporate zinc salts in dentifrice formulations.

Dissolvable films are capable of entrapping actives and other types of solid ingredients. However, the amount of solids can overload the film matrix creating a limit on the amount of solids it can contain. This creates a barrier as to how much can be loaded into the film and can increase the cost of films used in products Thus, there is an ongoing need for new oral and personal care compositions, and methods of their use.

SUMMARY

The present invention provides, in various embodiments, oral and personal care compositions comprising a film entrained in a carrier, in which the film includes a relatively high concentration of nonionic surfactants such as polysorbates. In one embodiment, the film is provided as a plurality of film fragments. In various embodiments, the present invention provides compositions comprising a plurality of lamellar fragments in a carrier.

In one embodiment, the oral care composition comprises a film entrained in a carrier, in which the film comprises a nonionic surfactant in an amount from 5% by weight of the film to 20% by weight of the film. Increasing the solid loading in the film formula increases the delivery of actives per area which is important for delivering superior efficacy.

The embodiments also provide methods for making the film and methods for administering an active compound to a human or animal subject in need thereof, the method including topically applying to the subject an oral care composition comprising a film entrained in a carrier, wherein the film comprises an nonionic surfactant in an amount from 5% by weight of the film to 20% by weight of the film. In various methods, such methods further comprise disrupting the film after the topical application.

Compositions and methods of this invention afford benefits over compositions and methods among those known in the art. Such benefits include one or more of increased consumer acceptability, improved amounts of available actives, decreased adverse reactions brought about by the presence of actives, enhanced aesthetics, improved stability for active or other functional materials, and controlled delivery of active materials. Further benefits and embodiments of the present invention are apparent from the description set forth herein.

DESCRIPTION

The present invention provides compositions and methods for administration to, or use with, a human or other animal subject. Preferably, specific materials and compositions to be used in this invention are, accordingly, pharmaceutically- or cosmetically-acceptable. As used herein, such a "pharmaceutically acceptable" or "cosmetically acceptable" component is one that is suitable for use with humans and/or animals to provide the desired therapeutic, sensory, decorative, or cosmetic benefit without undue adverse side effects (such as toxicity, astringent taste, irritation, and allergic response) commensurate with a reasonable benefit/risk ratio. The following definitions and non-limiting guidelines must be considered in reading and interpreting the description of this invention set forth herein.

The headings (such as "Introduction" and "Summary,") used herein are intended only for general organization of topics within the disclosure of the invention, and are not intended to limit the disclosure of the invention or any aspect thereof. In particular, subject matter disclosed in the "Introduction" may include aspects of technology within the scope of the invention, and may not constitute a recitation of prior art. Subject matter disclosed in the "Summary" is not an exhaustive or complete disclosure of the entire scope of the invention or any embodiments thereof.

The citation of references herein does not constitute an admission that those references are prior art or have any relevance to the patentability of the invention disclosed herein. All references cited in the Description section of this specification are hereby incorporated by reference in their entirety.

The description and specific examples, while indicating embodiments of the invention, are intended for purposes of illustration only and are not intended to limit the scope of the invention. Recitation of multiple embodiments having stated features is not intended to exclude other embodiments having additional features, or other embodiments incorporating different combinations of the stated features. Specific Examples are provided for illustrative purposes of how to make, use and practice the compositions and methods of this invention and, unless explicitly stated to recite activities that have been done (i.e., using the past tense), are not intended to be a representation that given embodiments of this invention have, or have not, been performed.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention. As used herein, the word "include," and its variants, is intended to be non-limiting, such that recitation of items in a list is not to the exclusion of other like items that may also be useful in the materials, compositions, devices, and methods of this invention. In a similar manner, the description of certain advantages or disadvantages of known materials and methods is not intended to limit the scope of the embodiments to their exclusion. Indeed, certain embodiments may include one or more known materials or methods, without suffering from the disadvantages discussed herein.

As used herein, the term "comprising" means that other steps and other components that do not affect the end result may be utilized. The term "comprising" encompasses the expressions "consisting of," and "consisting essentially of." The expression "effective amount," as used herein denotes an amount of a compound or composition sufficient to significantly induce a positive benefit, preferably an oral health benefit, but low enough to avoid serious side effects, i.e., to provide a reasonable benefit to risk ratio, within the sound judgment of a person having ordinary skill in the art. The use of singular identifiers such as "the," "a," or "an" is not intended to be limiting solely to the use of a single component, but may include multiple components.

The oral care compositions of the various embodiments preferably are in the form of a dentifrice. The term "dentifrice" as used throughout this description, denotes a paste, gel, or liquid formulation. The dentifrice may be in any desired form, such as deep striped, surface striped, multi-layered, having a gel surround the paste, or any combinations thereof. The film contained in the oral care composition may be of any desired shape or structure, including multiple small strips, or one continuous strip.

The expressions "carrier" or "aqueous carrier" as used throughout this description denote any safe and effective materials for use herein. Such materials include, for example, thickening agents, humectants, ionic active ingredients, buffering agents, anticalculus agents, abrasive polishing materials, peroxide sources, alkali metal bicarbonate salts, surfactants, titanium dioxide, coloring agents, flavor systems, sweetening agents, antimicrobial agents, herbal agents, desensitizing agents, stain reducing agents, and mixtures thereof.

All percentages and ratios used herein are by weight of the oral care composition, unless otherwise specified. All measurements are made at 25° C., unless otherwise specified.

The present invention provides oral or personal care compositions comprising a film entrained in a carrier, wherein the film comprises a relatively high concentration of nonionic surfactants such as polysorbates. As referred to herein, an "oral or personal care composition" is any composition that is suitable for administration or application to a human or animal subject for enhancing the health, hygiene or appearance of the subject, including the prevention or treatment of any physiologic condition or disorder, and providing sensory, decorative or cosmetic benefits and combinations thereof. Compositions among those provided herein include oral care compositions, skin care compositions, hair care composition, topical pharmaceutical compositions, and ocular compositions. By "oral care composition" as used herein is meant a composition for which the intended use can include oral care, oral hygiene, or oral appearance, or for which the intended method of use can comprise administration to the oral cavity.

Embodiments of this invention comprise a film. As referred to herein, a "film" is a material having a substantially lamellar structure. A "lamellar" structure has, or is capable of having, a size in one or two dimensions (e.g., the x- or y-dimensions) that is substantially greater than the thickness of the structure in a third dimension (e.g., the z-direction). Lamellar structures among those useful herein include those that are substantially planar, layered, or lamelliform. In one embodiment, the lamellar structure is substantially planar, having a size in both the x- and y-dimensions that is substantially greater than the z-direction. In other embodiments, the lamellar structure is non-planar. In one embodiment, a film of this intention comprises a substantially continuous surface that can appear as a substantially flat surface, although in some embodiments the film is deformed. In such embodiments, the film can have any of a number of shapes, including having a smooth curved surface.

Films among those useful herein may be rigid or plastic, comprising any of a variety of materials, including materials selected from the group consisting of film forming materials, clays, waxes, and mixtures thereof. In one embodiment, the film comprises a film forming polymer. Film forming polymers among those useful herein include materials selected from the group consisting of water soluble polymers, water dispersible polymers, water insoluble polymers, and mixtures thereof.

In some embodiments, a film comprises at least one film forming material. In certain embodiments, a film forming material is a polymer. Polymers useful herein include hydrophilic polymers and hydrophobic polymers. In certain embodiments, the polymer is a water soluble polymer. In some embodiments, the polymer is a water soluble, breakable polymer that dissolves during use, such as, for example, during toothbrushing. The dissolution can occur as a result of, for example, shearing and/or exposure to a solvent comprising a high concentration of water, such as saliva. In some embodiments, the polymer is insoluble but breakable in water by being dispersible, i.e., the polymer breaks down into small fragments, for example, as a result of shearing. In some embodiments, a polymer is insoluble but swellable. In configurations in which a polymer does not break down during use, the polymer can be a water-repellant polymer or an aqueous-stable hydrophilic polymer such as certain types of cellulose, for example paper. In some embodiments, a film fragment can comprise a mixture of film forming materials.

Water soluble polymers among those useful herein include cellulose ethers, methacrylates, polyvinylpyrollidone, and mixtures thereof. In one embodiment, the polymer is a cellulose ether, including those selected from the group consisting of hydroxyalkyl cellulose polymers such as hydroxypropyl methyl cellulose (HPMC), hydroxypropyl cellulose, hyrdoxyethyl cellulose, methyl cellulose, carboxymethyl cellulose, and mixtures thereof. Other polymers among those useful herein include polyvinylpyrrolidone, cross-linked polyvinyl pyrrolidone, polyvinylpyrrolidone-vinyl acetate copolymer, polyvinylalcohol, polyacrylic acid, poly acrylate polymer, cross-linked polyacrylate polymer, cross-linked polyacrylic acid (e.g, Carbopol®), polyethylene oxide, polyethylene glycol, poly vinylalkyl ether-maleic acid copolymer (such as Gantrez®) and carboxy vinyl polymer; natural gums such as sodium alginate, carrageenan, xantham gum, gum acacia, arabic gum, guar gum, pullulan, agar, chitin, chitosan, pectin, karaya gum, zein, hordein, gliadin, locust bean gum, tragacantha and other polysaccharides; starches such as maltodextrin, amylose, high amylose starch, corn starch, potato starch, rice starch, tapioca starch, pea starch, sweet potato starch, barley starch, wheat starch, waxy corn starch, modified starch (e.g. hydroxypropylated high amylose starch), dextrin, levan, elsinan and gluten; and proteins such as collagen, whey protein isolate, casein, milk protein, soy protein and gelatin.

Non-limiting examples of water dispersable and swellable polymers include modified starch, alginate esters, divalent or multivalent ion salts of alginates. Non-limiting examples of water insoluble polymers include polymers soluble in at least one organic solvent, such as cellulose acetate, cellulose nitrate, ethylene-vinyl acetate copolymers, vinyl acetate homopolymer, ethyl cellulose, butyl cellulose, isopropyl cellulose, shellac, silicone polymer (e.g. dimethylsilicone), PMMA (poly methyl methacrylate), cellulose acetate phthalate and natural or synthetic rubber; polymers insoluble in organic solvents, such as cellulose, polyethylene, polypropylene, polyesters, polyurethane and nylon.

The films useful in the various embodiments can be made in accordance with the methods described in U.S. Pat. No. 6,669,929, and U.S. Patent Application Publication No. 2003/0053962, the disclosures of which are incorporated by reference herein in their entirety. The nonionic surfactants contained within the film can be incorporated into the film during film manufacture using techniques known in the art. A person having ordinary skill in the art will be capable of making the film containing the high concentration of nonionic surfactants, using the guidelines provided herein.

The polymer matrix used in many dissolvable films, which are preferred in certain embodiments, has a limited capacity of the amount of solids it can hold. This creates a barrier as to how much can be loaded into the film and can increase the cost of films used in products. Certain formulation modifications can be performed, however, to increase the integrity of the film matrix to hold high loadings of solids. The present inventors have discovered that by increasing the amount of nonionic surfactants, more actives can be loaded into the film than could be done previously. A film having a higher concentration of actives allows more actives per area to be delivered, and also reduces the amount of film needed to deliver these higher amounts. The improved higher loading film formula provides higher deposition onto surfaces for superior efficacy. Also, improving the film formulation to hold a higher loading of actives can reduce the amount of total film needed in a product, while at the same time, delivering the same efficacy as with a lower loading of film. Without wishing to be bound by any theory of operation, the present inventors believe that the nonionic surfactants operate to help other ingredients dissolve into a solvent and aid in the formation of emulsions by reducing the surface tension of the substances to be emulsified. In addition, the nonionic surfactants do not interfere with other ingredients in the formula as is possible with anionic and cationic surfactants. As such, many different active ingredients may be used in a formulation with nonionic surfactants.

Preferred nonionic surfactants include polysorbates such as polysorbate 20, 40, 60, 80, or combinations thereof. Particularly preferred embodiments include polysorbate 80. Typical concentrations of polysorbates previously used in dissolvable film formulations are around 2% dry weight to aid in film disintegration. The inventors have discovered that by increasing the concentration of nonionic surfactants in the film formula, a higher loading of solids can be formulated and the speed of disintegration is not affected because of the solids loading. The amount of nonionic surfactants included in a film can vary from 5% by weight of the film to 20% by weight of the film, preferably from 10% by weight of the film to 18% by weight of the film, and most preferably 14% by weight of the film.

The amount of solids included in the film can vary from 20% to 65% by weight of the film, preferably from 30% to 55% by weight of the film, and most preferably 45% by weight of the film. The amount of film included in the oral composition also can vary anywhere from 0.1% to 5.0%, more preferably from 0.25% to 3.0%, and most preferably from 0.5% to 2.0% by weight. The amount of solids employed in the overall oral composition therefore can vary from 0.02% to 3.25%, based on the total weight of the composition, typically from 0.08% to 1.5%, based on the total weight of the oral care composition.

In various embodiments, the oral care compositions comprise a plurality of lamellar film fragments entrained in a carrier. In one embodiment, the composition comprises a film, wherein the film comprises lamellar fragments of the film material. In one embodiment, the composition comprises a carrier having distributed therein a plurality of lamellar fragments, wherein the fragments comprise a matrix and a therapeutic active. In one such embodiment, the matrix comprises a film. Such fragments may be of any of a variety of shapes or forms, including semi-solid or solid discrete portions, fragments, particles, flakes, or combinations thereof. In various embodiments, the film comprises a first plurality of fragments and a second plurality of fragments, wherein the first plurality of fragments differ in composition or appearance from the second plurality of fragments. Such difference in composition or appearance can be in any aspect of the composition of the fragment (e.g., different film components, different functional material, different formulation colorant), different appearance (e.g., shape, color, texture, refractive index, reflective index), or combinations thereof.

In various embodiments, the fragments exhibit perceivable contrast with the carrier. The perceivable contrast can be sensory contrast, such as optical contrast, tactile contrast, taste contrast, or olfactory contrast. In some configurations, optical contrast can be color contrast, or a difference in refractive index or reflective index. In some configurations, color contrast can be imparted by one or more colorants that comprise different components of the composition. In various embodiments, the present invention provides compositions comprising a plurality of film fragments in a carrier, wherein said fragments are visibly discernable. As referred to herein, "visibly discernable" refers to one or more characteristics of a fragment which cause the fragment to have a different physical appearance, preferably to the naked eye, relative to the carrier in which the fragment is entrained. Such characteristics include color, opacity, refractive index, reflective index, size, shape, and combinations thereof.

In various embodiments, the fragments have a non-random shape. In one embodiment, a "non-random" shape is a shape which results from a manufacturing process of shaping, cutting, or other forming process by which a specific shape is imparted to a fragment. In such embodiments, a non-random shape is distinguished from such shapes that result from simple precipitation or grinding of a material. In one embodiment, a "non-random" shape is "repeating," wherein the composition comprises a plurality of fragments have substantially the same shape. Such repeating shape may have any of a variety of forms, and may be selected based on a variety of aesthetic or functional criteria. In certain embodiments, the shape of a film fragment can be a recognizable shape. In certain embodiments, a film fragment can comprise a nonrandom shape. Such shapes include simple geometric shapes, such as polygons and elliptical shapes, such as triangles, quadrilaterals (such as a square, a rectangle, a rhombus), pentagons, hexagons, oval, and circles. In one embodiment, the repeating shape is a square. Repeating shapes include, in other embodiments, shapes that are representative of figures or animate or inanimate objects, such as stars, hearts, gems, flowers, trees, shamrocks, a letter of an alphabet, numbers, animals, people, and faces. In various embodiments, the composition comprises a single repeating shape. In other embodiments, the composition comprises a plurality of fragments having a plurality of repeating shapes. In one embodiment, the compositions of the present invention comprise a plurality of first film fragments having a first repeated shape and a plurality of second film fragments having a second repeated shape, wherein the first repeated shape is different from the second repeated shape.

In various embodiments, the size of the fragments is not critical, and may be determined pursuant to any of a variety of criteria, including manufacturing convenience, affect on visual appearance, surface area, affect on texture in the composition, and combinations thereof. In some embodiments, the film fragments can be up to 1 inch (25.4 mm) in length in the longest dimension. As referred to herein, "long dimension" is the dimension of a fragment in length or width (i.e., in the x- and y-dimensions, as the fragment is, or is deformed to be, in a planar shape) in a dimension substantially perpendicular to the "thickness" or shortest dimension of the fragment (i.e., the z-dimension). It is understood that in various embodiments comprising a plurality of fragments, the fragments may be present in a range of sizes due to a variety of factors, including random variation in size, manufacturing tolerances, and intentional sizing or mixing of the fragments through sieving or similar means. As referred to herein, sizes refer to the average size of fragments in a given plurality of fragments.

In various embodiments, the fragments are from 0.2 mm to 15 mm in long dimension. In various embodiments, the long dimension of the fragments is from 0.2 mm to 10 mm, from 0.5 mm to 10 mm, from 0.8 mm to 8 mm, from 0.9 mm to 5 mm, from 1.0 mm to 5 mm, or from 1.5 mm to 2.5 mm. In some embodiments, the long dimension of the fragments is at least 3 mm, and can be from 6 mm to 13 mm. In certain embodiments, a plurality of film fragments are greater than 600 microns in the longest dimension. In certain embodiments, a plurality of film fragments are greater than 1 millimeter in the longest dimension.

In various embodiments, the fragments of the present invention have a thickness of from 1 mil (thousandth of an inch, 25.4 microns) to 3 mils (76.2 microns). In various embodiments, the fragments have a thickness of less than 4 mils or less than 100 microns and from 0.1 mils (2.54 microns) up to 10 mils (254 microns), from 0.5 mils (12.7 microns) up to 5 mils (127 microns), from 1.4 mils (35.6 microns) to 2.0 mils (50.8 microns).

In some embodiments, the compositions of the present invention comprise fragments having an aspect ratio of at least 5:1. As referred to herein, "aspect ratio" of a fragment is the ratio of the diameter of the smallest imaginary sphere that can enclose the object to the diameter of the largest imaginary sphere that can be completely inside the object and tangent to the surfaces of the object. For example, the aspect ratio of a sphere is 1:1; in another example, the aspect ratio of a cylinder that is 2 inches (50.8 mm) long and ¼ inch (6.35 mm) in diameter is slightly over 8:1; in yet another example, a film fragment of the present invention that is 1 mil (25.4 microns) in thickness, 1 inch (25.4 mm) in length, and 1 inch (25.4 mm) wide has an aspect ratio of 1414:1.

In some embodiments, the compositions of the present invention comprise fragments having an aspect ratio of at least 10:1. In various embodiments, the fragments have an aspect ratio of from 5:1 to 10,000:1, from 5:1 to 500:1, from 10:1 to 1,000:1, from 10:1 to 100:1, from 20:1 to 100:1, or from 25:1 to 35:1.

In various embodiments, the film comprises a formulation colorant that imparts a color to the film, the composition, or both. In various embodiments, the film fragments contrast with the carrier, and are white, black, or of any color that is visible against or contrasts with the carrier background. Formulation colorants among those useful herein include non-toxic water soluble dyes or pigment, such as, for example, metallic oxide "lakes." In certain embodiments, the colorant is approved for incorporation into a food or drug by a regulatory agency, such as FD&C or D&C pigments and dyes approved by the FDA for use in the United States. Colorants among those useful herein include FD&C Red No. 3 (sodium salt of tetraiodofluorescein), Food Red 17, disodium salt of 6-hydroxy-5-{(2-methoxy-5-methyl-4-sulphophenyl)azo}-2-naphthalenesulfonic acid, Food Yellow 13, sodium salt of a mixture of the mono and disulphonic acids of quinophtalone or 2-(2-quinolyl) indanedione, FD&C Yellow No. (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4-hydroxy-2-sulfoniumphenyl)-methylene}-[1-(N-ethyl-N-p-sulfobenzyl)-Δ-3,5-cyclohexadienimine], FD&C Blue No. 1 (disodium salt of dibenzyldiethyldiaminotriphenylcarbinol trisulfonic acid anhydrite), FD&C Blue No. 2 (sodium salt of disulfonic acid of indigotin), and mixtures thereof in various proportions. In one embodiment, the colorant comprises a water insoluble inorganic pigment, such as titanium dioxide, chromium oxide green, phthalocyanine green, ultramarine blue, ferric oxide, or a water insoluble dye lake. In some embodiments, dye lakes include calcium or aluminum salts of an FD&C dye such as FD&C Green #1 lake, FD&C Blue #2 lake, D&C Red #30 lake or FD&C # Yellow 15 lake. In certain embodiments, a water soluble dye, such as, for example, FD&C Blue #1, is contained within a water-insoluble polymer such as, for example polyethylene such as that found in polyethylene beads (e.g., Microblue Spectrabeads, sold by Micropowders, Inc.). In certain embodiments, the film comprises a dye such as D&C Red #30. In certain embodiments, a white colorant is used, for example titanium dioxide ($TiO_2$), titanium dioxide coated mica (e.g., Timiron), a mineral, or a clay. In certain embodiments, the colorant is a non-bleeding dye. In various embodiments, the film comprises a colorant at a level of from 0.5% to 20% by weight of the film, or from 1% to 15% by weight of the film, or from 3% to 12% by weight of the film. In one embodiment, the compositions of the present invention comprise a first plurality of film fragments comprising a first color, and a second plurality of film fragments comprising a second color. Preferably, the second color is different than the first color.

The film of the present invention, in various embodiments, disintegrates during use of the composition. In other embodiments, the film does not disintegrate during use of the composition. In some embodiments, the film releases a material, such as a therapeutic active, into the carrier. As referred to herein, "disintegrate" refers to physical disruption of the film or fragment material, so as to produce a film or film fragments of reduced size compared to the original film. Such disruption may be through mechanical, chemical, or physical-chemical means. The disintegration can result, for example, from shearing, grinding, or exposure to elevated temperatures during use. In various dentifrice embodiments of the present invention, such disintegration results from brushing of the composition on the teeth of the subject using the composition. In one embodiment, the film disintegrates so as to release a therapeutic active. In some embodiments, a film fragment can disintegrate into small pieces that are not visually discernable. In some embodiments, the film fragments disintegrate to collectively form a colloid or gel.

In various embodiments, the film may comprise therapeutic actives. As referred to herein, a therapeutic active is a material that is useful for the prevention or treatment of a physiological disorder or condition. Such disorders or conditions include those of the oral cavity (including the teeth and gingiva), skin, hair, and eyes. The specific therapeutic active is preferably determined according to the desired utility of the composition. Such actives include the following.

A. antimicrobial agents, such as triclosan, cetyl pyridium chloride, domiphen bromide, quaternary ammonium salts, sanguinarine, fluorides, alexidine, octonidine, EDTA, essential oils such as thymol, methyl salicylate, eucalyptol and menthol, and zinc compounds, and the like, B. non-steroidal anti-inflammatory drugs, such as aspirin, acetaminophen, ibuprofen, ketoprofen, diflunisal, fenoprofen calcium, naproxen, tolmetin sodium, indomethacin, and the like, C. anti-tussives, such as benzonatate, caramiphen edisylate, menthol, dextromethorphan hydrobromide, chlophedianol hydrochloride, and the like, D. decongestants, such as pseudoephedrine hydrochloride, phenylepherine, phenylpropanolamine, pseudoephedrine sulfate, and the like, E. anti-histamines, such as brompheniramine maleate, chlorpheniramine maleate, carbinoxamine maleate, clemastine fumarate, dexchlorpheniramine maleate, diphenhydramine hydrochloride, diphenylpyraline hydrochloride, azatadine meleate, diphenhydramine citrate, doxylamine succinate, promethazine hydrochloride, pyrilamine maleate, tripelennamine citrate, triprolidine hydrochloride, acrivastine, loratadine, brompheniramine, dexbrompheniramine, and the like, F. expectorants, such as guaifenesin, ipecac, potassium iodide, terpin hydrate, and the like, G. anti-diarrheals, such a loperamide, and the like, H. $H_2$-antagonists, such as famotidine, ranitidine, and the like; and I. proton pump inhibitors, such as omeprazole, lansoprazole, and the like, J. general nonselective CNS depressants, such as aliphatic alcohols, barbiturates and the like, K. general nonselective CNS stimulants such as caffeine, nicotine, strychnine, picrotoxin, pentylenetetrazol and the like, L. drugs that selectively modify CNS function such as phenyhydantoin, phenobarbital, primidone, carbamazepine, ethosuximide, methsuximide, phensuximide, trimethadione, diazepam, benzodiazepines, phenacemide, pheneturide, acetazolamide, sulthiame, bromide, and the like, M. antiparkinsonism drugs such as levodopa, amantadine and the like, N. narcotic-analgesics such as morphine, heroin, hydromorphone, metopon, oxymorphone, levorphanol, codeine, hydrocodone, xycodone, nalorphine, naloxone, naltrexone and the like, O. analgesic-antipyretics such as salicylates, phenylbutazone, indomethacin, phenacetin and the like, and P. psychopharmacological drugs such as chlorpromazine, methotrimeprazine, haloperidol, clozapine, reserpine, imipramine, tranylcypromine, phenelzine, lithium and the like.

The amount of medicament that can be used in the films can be dependent upon the dose needed to provide an effective amount of the medicament.

In various embodiments, therapeutic actives useful herein include anticaries agents, tartar control agents, antiplaque agents, periodontal actives, breath freshening agents, malodour control agents, whitening agents, antibacterials, steroids, anti-inflammatory agents, vitamins, proteins, conditioning agents, moisturizers, antiperspirant actives, deodorant actives, anesthetics, and mixtures thereof.

In certain oral care embodiments, the film or the oral care composition may comprise an oral care active, which is useful for the prevention or treatment of an oral care disorder or condition. Oral care actives among those useful herein include abrasives, anticaries agents, tartar control agents, antiplaque agents, periodontal actives, breath freshening agents, malodour control agents, tooth desensitizers, salivary stimulants, whitening agents, and combinations thereof. Active materials among those useful herein are described in U.S. Pat. No. 6,596,298, Leung et al.

Tartar control agents among those useful herein include dialkali or tetraalkali metal pyrophosphate salts such as $Na_4P_2O_7$, $K_4P_2O_7$, $Na_2K_2P_2O_7$, $Na_2H_2P_2O_7$ and $K_2H_2P_2O_7$; long chain polyphosphates such as sodium hexametaphosphate; and cyclic phosphates such as sodium trimetaphosphate. In some configurations, a polyphosphate is a beta.-phase calcium pyrophosphate, such as disclosed in U.S. Pat. No. 6,241,974, White, Jr. In some embodiments, the film comprises an anticalculus agent at a level of 15 to 20% by weight of the film.

Odor reducing agents useful herein include sulfur precipitating agents. Such sulfur-precipitating agents include metal salts, such as a copper salt or a zinc salt. Such salts include copper gluconate, zinc citrate and zinc gluconate. These zinc salts can be used in combination or in addition to the zinc compounds included in the film. In various embodiments, the film comprises sulfur precipitating agents at a level of from 0.01 to 30% by weight of film, from 2% to 2.5% by weight of film, or 10% to 20% by weight of film.

In a certain embodiments, the film and/or oral composition may include a saliva stimulating agent (a "succulent"). Such agents include those disclosed in U.S. Pat. No. 4,820,506, Kleinberg et al. In some configurations, a saliva stimulating agent can include a food acid such as citric, lactic, malic, succinic, ascorbic, adipic, fumaric and tartaric acids. In various embodiments, the film comprises a saliva stimulating agent at a level of from 0.01 to 12% by weight of the film, from 1% to 10% by weight of the film, or from 2.5% to 6% by weight of the film. In some embodiments, a saliva stimulating agent can be used in the amelioration of dry mouth.

In certain oral care embodiments, the film comprises other active materials, such as antibacterial agents such as magnolia extract, triclosan, grapeseed extract, thymol, methyl salicylate, eucalyptol, menthol, hop acids, cetyl pyridinium chloride, (including CPC/Zn and CPC+enzymes) and usnic acid; anti-inflammatory agents such a breath freshening agents (for example zinc gluconate, zinc citrate, zinc chlorite and alpha ionone); tooth desensitizers such as potassium nitrate, desensitizing polymers, and desensitizing minerals; anti-inflammatory agents such as magnolia extract, ursolic acid; aloe, and cranberry extract; vitamins such as pantheon, retinyl palmitate, folic acid, tocopherol acetate and Vitamin A; herbs or herbal extracts such as rosemary, oregano, *chamomilla recutita, mentha piperita, salvia officinalis*, or *commiphora* and *myrrha*; proteins, such as milk proteins and enzymes such as peroxide-producing enzymes, amylase, plaque—disrupting agents such as papain, glucoamylase, glucose oxidase, and "next generation" enzymes; whitening agents such as hydrogen peroxide, urea peroxide and phosphate salts; medicinals, such as aspirin (acetyl salicylic acid), caffeine, and benzocaine; probiotics; abrasives such as silicas (including high cleaning silica); anti-caries agents such as stannous salts (e.g., stannous fluoride) or amino fluoride; a nitric oxide synthase inhibitor such as guanidinoethyldisulfide; calcium; antiattachment ingredients, such as polyumylphosphonic acid; preservatives such as Solbrol® (Bayer Chemicals AG); silicones; chlorophyll compounds, anti-leukoplakia agents such as beta-carotene; anti-oxidants such as Vitamin E; and combinations thereof. In some embodiments, the films comprise such active materials at a concentration of 0.01 to 30% by weight of film, from 2% to 25% by weight of the film, or from 10% to 20% by weight of film.

The oral compositions of certain embodiments include a zinc compound in a film that provides a source of zinc ions. The zinc compound can be a soluble or sparingly soluble compound of zinc with inorganic or organic counter ions. Examples include the fluoride, chloride, chlorofluoride, acetate, hexafluorozirconate, sulfate, tartrate, gluconate, citrate, lactate, malate, glycinate, pyrophosphate, metaphosphate, oxalate, phosphate, carbonate salts, and oxides of zinc. Preferably, the zinc compound is zinc oxide, and is used as a replacement for conventional anti-bacterial agents such as triclosan.

Zinc ions are derived from the zinc compound present in the film in the dentifrice composition in an effective amount. An effective amount of zinc ions is defined as from at least 1000 ppm zinc ion, preferably 2,000 ppm to 15,000 ppm. More preferably, zinc ions are present in an amount from 3,000 ppm to 13,000 ppm and even more preferably from 4,000 ppm to 10,000 ppm. This is the total amount of zinc ions that is present in the compositions for delivery to the tooth surface.

Examples of suitable zinc compounds that serve as zinc ion sources are zinc oxide, zinc sulfate, zinc chloride, zinc citrate, zinc lactate, zinc gluconate, zinc malate, zinc tartrate, zinc carbonate, zinc phosphate, and other salts listed in U.S. Pat. No. 4,022,880.

In certain embodiments, the film and/or oral care composition includes a preservative. A preservative can be added in amounts from 0.001 wt % to 5 wt %, preferably from 0.01 wt % to 1 wt % of the film. Non-limiting examples of preservatives include sodium benzoate and potassium sorbate.

In certain embodiments, the entrainment of the therapeutic actives in the film matrix suspended in the dentifrice or other composition isolates these agents from interaction with reactive ingredients present in the composition so that the agents are maintained substantially separate from the reactive composition ingredients during manufacture and storage while subsequently being released from the film matrix when the composition is used. Isolation not only avoids adverse reactions that may occur between the therapeutic actives and other components that are present in the carrier material, but also avoids dissolution of the therapeutic actives and premature release of actives.

The compositions of the present invention comprise a carrier in which a film, or fragments, is entrained. As referred to herein, a "carrier" is any material or composition in which a film can be entrained and is suitable for administration or application to the human or animal subject to whom the composition is administered or applied. As referred to herein, "entrained" refers to the embedding or suspension of a film in a carrier. In various embodiments comprising a plurality of fragments, such fragments may be entrained by embedding, suspension, dispersion or other distribution of the fragments in the carrier. In various embodiments, the fragments are distributed substantially homogenously throughout the carrier. In other embodiments, the fragments are not distributed homogenously in the carrier. In certain embodiments, the distribution of a plurality of film fragments is substantially isotropic within the carrier. Dentifrice compositions that include a plurality of film fragments dispersed or suspended in a carrier are commercially available under the tradename Max Fresh® or Max White®, from Colgate-Palmolive Company, New York, N.Y.

The compositions of the embodiments may be described as comprising two phases, wherein one phase comprises a carrier and a second phase comprises the aforementioned film or fragment. The term "phase" as used herein denotes a physical phase as understood in the physical and material sciences, i.e., a portion of a material whose properties and composition are uniform. However, a phase as used herein can be discontinuous, i.e., a phase can comprise a plurality of separate components. For example, a plurality of polymer film fragments of identical composition is considered to comprise a single phase. In some embodiments, a film fragment can be entirely embedded within the material comprising the first phase, or totally or partially exposed on the surface of the first phase. For example, if the composition is a dentifrice comprising both a gel and film fragments, a film fragment can be totally surrounded by the gel, or partially or totally exposed on the surface of the gel. In certain embodiments, compositions comprise more than two phases. Such multi-phase compositions include those having two carriers, each of which contributes a phase to the composition, in addition to film fragments as described herein. Other multi-phase compositions include those having a single carrier and two or more pluralities of fragments, wherein the pluralities of fragments have differing compositions.

In various embodiments, the carrier is a liquid, semi-solid or solid. A "liquid" can be a liquid of low or high viscosity. A liquid can be a liquid such that flow is imperceptible under ambient conditions. For example, a soap, such as an ordinary bar of hand soap, can be considered a liquid herein. A liquid can be a thixotropic liquid. A "semi-solid" as used herein can be a gel, a colloid, or a gum. As used herein, semi-solids and liquids are fluids distinguished on the basis of viscosity: a semi-solid is a high viscosity fluid, while a liquid has lower viscosity. There is no definitive dividing line between these two types of fluids. A semi-solid can, in certain embodiments, have a viscosity as high as thousands of mPa·s. Carriers among those useful herein include liquids, pastes, ointments, and gels, and can be transparent, translucent or opaque.

In certain embodiments, the compositions of the present invention are oral care compositions, suitable for administration to the oral cavity. Such compositions include dentifrices, mouthwashes, dental gels, lozenges, beads, gums, oral strips, mints, liquid toothpastes, sprays, paint-on gels, lip balms, whitening strips, breath strips, oral chews, and combinations thereof. An oral care composition disclosed herein can be used, for example, for cavity prevention, whitening, plaque prevention or reduction, gingivitis prevention or reduction, tartar control, sensitivity prevention or reduction, or breath malodor prevention or reduction, and stain prevention.

The specific composition of the carrier preferably depends on the intended use of the composition. In various embodiments, the carrier is aqueous, comprising from 5% to 95% water or from 10% to 70% water. In other embodiments, the carrier is substantially non-aqueous. In a dentifrice carrier, water content can be from 5% to 70%, from 10% to 50%, or from 20% to 40%. When the presence of water will cause the film to disintegrate, it is particularly preferred that the dried film contain no free water, in which the amount of water is substantially 0%, or negligible.

The carrier may comprise any of a variety of materials, including emulsifiers, thickeners, fillers, and preservatives. In some embodiments, the carrier may include a functional or active material, such as those described above. In some embodiments, the carrier comprises the same functional material as the film.

In one embodiment, the carrier is suitable for use as a dentifrice. In some embodiments, the carrier comprises a humectant, such as glycerine, sorbitol or an alkylene glycol such as polyethylene glycol or propylene glycol. In some configurations, the carrier comprises a humectant at a level of from 10% to 80% by weight, or 20% to 60% by weight of the composition. Carrier compositions among those useful herein are disclosed in U.S. Pat. No. 5,695,746, Garlick, Jr., et al, and U.S. Pat. No. 4,839,157, Mei-King Ng et al.

In various dentifrice embodiments, the carrier comprises thickeners, gelling agents or combinations thereof. Thickeners or gelling agents useful herein include inorganic, natural or synthetic thickeners or gelling agents. In some configurations, the carrier comprises the thickener and gelling agent at total levels of from 0.10% to 15% by weight, or from 0.4% to 10% by weight of the composition. Examples of thickeners and gelling agents useful herein include inorganic thickening silicas such as: an amorphous silica, for example Zeodent® 165 (Huber Corporation); Irish moss; iota-carrageenan; gum tragacanth; or polyvinylpyrrolidone. In certain embodiments, the carrier comprises a polishing agent, such as a silica, a calcined alumina, sodium bicarbonate, calcium carbonate, dicalcium phosphate or calcium pyrophosphate. In various embodiments, the carrier can be a visually clear composition.

In various dentifrice embodiments, comprising a visually clear carrier, the composition comprises at least one polishing agent. Polishing agents among those useful herein include collodial silica, such as, for example, Zeodent® 115 (Huber Corporation), and alkali metal aluminosilicate complexes (i.e., a silica comprising alumina). In some configurations, a polishing agent can have a refractive index close to that of a gelling agent combined with water and/or humectant. In various embodiments, the carrier comprises the polishing agent at a level of from 5% to 70% by weight of the composition.

In certain dentifrices, the carrier comprises additional surfactants or mixture of surfactants. Surfactants among those useful herein include water-soluble salts of at least one higher fatty acid monoglyceride monosulfate, such as the sodium salt of the monsulfated monoglyceride of hydrogenated coconut oil fatty acids; cocamidopropyl betaine; a higher alkyl sulfate such as sodium lauryl sulfate; an alkyl aryl sulfonate such as sodium dodecyl benzene sulfonate; a higher alkyl sulfoacetate; sodium lauryl sulfoacetate; a higher fatty acid ester of 1,2-dihydroxy propane sulfonate; and a substantially saturated higher aliphatic acyl amides of a lower aliphatic amino carboxylic acid, such as those having 12 to 16 carbons in the fatty acid, alkyl or acyl radicals; and mixtures thereof. Amides can be, for example, N-lauroyl sarcosine, and the sodium, potassium, and ethanolamine salts of N-lauroyl, N-myristoyl, or N-palmitoyl sarcosine. In various embodiments the carrier comprises the surfactant at a level of from 0.3% to 5% by weight of composition, or 0.5% to 3% by weight of composition.

The present invention also provides methods for making a dentifrice carrier. In one embodiment, water and at least one humectant are dispersed in a conventional mixer until a first homogeneous gel phase is formed. A polishing agent is added into the first homogeneous gel phase. The first homogeneous gel phase and the polishing agent are mixed until a second homogeneous gel phase is formed. A thickener, flavorant and surfactants are added to the second homogeneous gel phase. These ingredients are mixed at high speed under vacuum of 20 to 100 mmHg.

The compositions of the present invention are preferably stable under normal conditions of storage. As referred to herein, "stable" refers to the lack of significant adverse effect on one, and preferably all, compositional attributes such as appearance, flavor, rheology, and chemical composition of the composition. Preferably, stability in the present compositions includes the compositional and physical stability of film (including fragments, if any) in the composition. In various embodiments a composition comprising a film is stable upon storage at ambient temperature for at least two years. It is understood, however, that in some embodiments, an otherwise stable film can disintegrate during use (as discussed above), for example, during toothbrushing using a dentifrice composition.

In certain embodiments, a composition can comprise, in addition to film fragments as described herein, two or more carriers, each of which contributes a phase to the composition. Such a composition can be stable to color bleeding. For example, a composition can include film fragments and a striped dentifrice such as that disclosed in U.S. Pat. No. 6,315,986, Wong et al. In certain embodiments, the film fragments can be of different color(s) than the stripe(s) for enhanced aesthetic appeal.

The embodiments also provides processes for making compositions comprising a film entrained in a carrier. In various embodiments, a plurality of fragments are combined with a carrier. In some configurations, a carrier and a plurality of film fragments can be mixed. In some configurations, the mixing can comprise slow stirring. In one preferred embodiment, the process for making the composition comprising a carrier having distributed therein a plurality of lamellar fragments includes:

(a) providing the carrier;
(b) adding lamellar fragments of a film containing a relatively high concentration of nonionic surfactants such as polysorbates to the carrier to form a mixture; and
(c) homogenizing the mixture.

The term "homogenizing" as used herein refers to the admixture of the fragments and the carrier so as to attain a substantially homogeneous distribution of fragments in the carrier. It should be noted, however, that the resulting composition still retains two-phase composition characteristics. Homogenizing may be accomplished using any of a variety of conventional homogenizers.

In another method, the film is added to a component of the carrier (e.g., to a humectant for a dentifrice). The remainder of the carrier then may be made, and the mixture of film then added to the carrier.

In various embodiments, the present invention provides methods for administering a functional material to a human or animal subject in need thereof, comprising topically applying to said subject a composition comprising a film entrained in a carrier, wherein the film includes a relatively high concentration of nonionic surfactants. As referred to herein, "administering" refers to any method by which a composition is applied on or administered to the subject. In various embodiments, the administration is topical, wherein the composition is applied to an external surface of the subject, such as to a surface of the oral cavity (e.g., teeth, gingival, and tongue).

The specific route and method of administration will depend, of course, on the intended use of the composition. In one embodiment, the method additionally comprises disrupting the film after topically applying the film. Such disruption may be accomplished by any of a variety of methods, including chemical and/or mechanical means. Chemical means include degradation of the film by contact with water or a material present at the site of administration (e.g., saliva in an oral care application). Physical means include agitation, grinding, and shear forces produced by application of physical energy to the composition during use (e.g., brushing in a dentifrice application).

In various embodiments, the present invention provides methods for the treatment of an oral care condition. As referred to herein, an "oral care condition" is any disorder or condition which can be prevented or treated by administration of a composition to the oral cavity, including disorders or conditions of the teeth, oral mucosa, gingiva and tongue. Such conditions include caries, gingivitis, periodontitis, and cosmetic conditions such as yellowing and malodour.

The embodiments described herein can be further understood by reference to the following non-limiting examples.

EXAMPLE 1

This example illustrates various formulations of polymeric films containing therapeutic actives and varying amounts of nonionic surfactants, in particular polysorbate 80.

TABLE 1

18% Menthol with 2% Polysorbate 80

| Raw Materials | Slurry Wt. % | Dry Wt. % |
|---|---|---|
| Water | 80.0 | — |
| Methocel E5 (HPMC) | 8.1 | 40.2 |
| Methocel E50 (HPMC) | 2.4 | 12.1 |
| Cornstarch | 3.2 | 16.1 |
| Menthol | 3.5 | 17.6 |
| Titanium Dioxide | 0.8 | 4.0 |
| Propylene Glycol | 1.6 | 8.0 |
| Polysorbate 80 (Tween 80) | 0.4 | 2.0 |
| Total: | 100 | 100 |

TABLE 2

51% Calcium Peroxide with 1.6% Polysorbate 80

| Raw Materials | Slurry Wt. % | Dry Wt. % |
|---|---|---|
| Water | 69.0 | — |
| Methocel E5 (HPMC) | 8.3 | 26.8 |
| Methocel E50 (HPMC) | 2.9 | 9.3 |
| Calcium Peroxide | 15.8 | 51.0 |
| Titanium Dioxide | 1.0 | 3.2 |
| Propylene Glycol | 2.5 | 8.1 |
| Polysorbate 80 (Tween 80) | 0.5 | 1.6 |
| Total: | 100 | 100 |

TABLE 3

45% Calcium Peroxide with 14% Polysorbate 80

| Raw Materials | Slurry Wt. % | Dry Wt. % |
|---|---|---|
| Water | 64.5 | — |
| Methocel E5 (HPMC) | 8.3 | 23.4 |

TABLE 3-continued

45% Calcium Peroxide with 14% Polysorbate 80

| Raw Materials | Slurry Wt. % | Dry Wt. % |
| --- | --- | --- |
| Methocel E50 (HPMC) | 2.9 | 8.2 |
| Calcium Peroxide | 15.8 | 44.5 |
| Titanium Dioxide | 1.0 | 2.8 |
| Propylene Glycol | 2.5 | 7.0 |
| Polysorbate 80 (Tween 80) | 5.0 | 14.1 |
| Total: | 100 | 100 |

TABLE 4

31% Calcium Peroxide plus 15% Zeodent 105 with 14% Polysorbate 80

| Raw Materials | Slurry Wt. % | Dry Wt. % |
| --- | --- | --- |
| Water | 63.5 | — |
| Methocel E5 (HPMC) | 8.3 | 22.7 |
| Methocel E50 (HPMC) | 2.9 | 8.0 |
| Calcium Peroxide | 11.3 | 31.0 |
| Titanium Dioxide | 1.0 | 2.7 |
| Zeodent 105 (silica) | 5.5 | 15.1 |
| Propylene Glycol | 2.5 | 6.8 |
| Polysorbate 80 (Tween 80) | 5.0 | 13.7 |
| Total: | 100 | 100 |

TABLE 5

5% Carbopol 974 with 10% Polysorbate 80

| Raw Materials | Slurry Wt. % | Dry Wt. % |
| --- | --- | --- |
| Water | 81.0 | — |
| Methocel E5 (HPMC) | 8.0 | 42.2 |
| Methocel E50 (HPMC) | 2.4 | 12.7 |
| Calcium Peroxide | 3.2 | 17.0 |
| Titanium Dioxide | 0.8 | 4.2 |
| Carbopol 974 | 1.0 | 5.0 |
| Propylene Glycol | 1.6 | 8.4 |
| Polysorbate 80 (Tween 80) | 2.0 | 10.5 |
| Total: | 100 | 100 |

Table 1 is a formula for a currently available commercial film product containing 2% by weight polysorbate 80 (commercially available in MaxFresh® toothpaste formulations, available from Colgate-Palmolive Company, New York, N.Y.). The film contains a low level of polysorbate 80 (2% wt) and does not contain a high loading of solids (17.6% wt menthol).

Table 2 is a formula for a whitening film that contains calcium peroxide as the whitening agent. This formulation has a low level of polysorbate 80 (1.6% wt) and a high level of calcium peroxide (51% wt). The film produced was not robust and cracked on drying.

Table 3 is a formula for a whitening film that contains calcium peroxide as the whitening agent. This formulation has an increased level of polysorbate 80 (14.1% wt) and a high level of calcium peroxide (45% wt). The film produced was robust and able to contain the high solids loading of calcium peroxide.

Table 4 is a formula for another whitening film that contains two whitening agents, calcium peroxide and Xeodent 105. The film contains an increased level of polysorbate 80 (13.7% wt) and a high level of calcium peroxide and Xeodent 105 (46% wt combined). The film produced was robust.

Table 5 is a formula for a mucoadhesive film that contains a mucoadhesive agent called Carbopol 974. The film contains an increased level of polysorbate 80 (10.5% wt) and the formula is also robust.

The examples and other embodiments described herein are exemplary and not intended to be limiting in describing the full scope of compositions and methods of this invention. Equivalent changes, modifications and variations of specific embodiments, materials, compositions and methods may be made within the scope of the present invention, with substantially similar results.

We claim:

1. An oral care composition comprising a film entrained in a carrier,
   wherein the film comprises
      a nonionic surfactant in an amount from 5% by weight of the film to 20% by weight of the film and
      a solid active ingredient in an amount from 30% by weight of the film to 55% by weight of the film, and
   wherein the film is present in an amount of from 0.1% to 5.0% by weight of the total weight of the composition.

2. The oral care composition of claim 1, wherein the composition is in the form of a dentifrice.

3. The oral care composition of claim 1, wherein the nonionic surfactant comprises a polysorbate.

4. The oral care composition of claim 3, wherein the polysorbate is selected from the group consisting of polysorbate 20, polysorbate 40, polysorbate 60, polysorbate 80, and combinations thereof.

5. The oral care composition of claim 4, wherein the polysorbate is polysorbate 80.

6. The oral care composition of claim 1, wherein the solid active ingredient comprises a therapeutic active.

7. The oral care composition of claim 6, wherein the therapeutic active is present in the film in an amount of from 30% by weight of the film to 55% by weight of the film.

8. The oral care composition of claim 1, wherein the film is present in an amount of from 0.25% to 3.0% by weight of the total weight of the composition.

9. The oral care composition of claim 8, wherein the film is present in an amount of from 0.5% to 2.0% by weight of the total weight of the composition.

10. A method of making an oral care composition comprising a film entrained in a carrier wherein the film comprises a nonionic surfactant in an amount from 5% by weight of the film to 20% by weight of the film and a solid active ingredient in an amount from 30% by weight of the film to 55% by weight of the film, and wherein the film is present in an amount of from 0.1% to 5.0% by weight of the total weight of the composition,
    the method comprising:
        (a) providing the carrier;
        (b) adding lamellar fragments of the film comprising the nonionic surfactant in an amount from 5% by weight of the film to 20% by weight of the film and the solid active ingredient in an amount from 30% by weight of the film to 55% by weight of the film; and
        (c) homogenizing the mixture.

11. The method of claim 10, wherein the nonionic surfactant is polysorbate 80.

12. The method of claim 10, wherein the solid active ingredient comprises a therapeutic active.

13. The method of claim 12, wherein the therapeutic active is present in the film in an amount of from 30% by weight of the film to 55% by weight of the film.

14. A method for administering an active to a human or animal subject in need thereof comprising topically applying to the subject an oral care composition comprising a film, wherein the film comprises a nonionic surfactant in an amount from 5% by weight of the film to 20% by weight of the film and a solid active ingredient in an amount from 30% by weight of the film to 55% by weight of the film, and wherein the film is present in an amount of from 0.1% to 5.0% by weight of the total weight of the composition.

15. The method of claim 14, further comprising disrupting the film after the topical application.

16. The method of claim 14, wherein the nonionic surfactant is polysorbate 80.

17. The method of claim 14, wherein the solid active ingredient comprises a therapeutic active.

18. The method of claim 17, wherein the therapeutic active is present in the film in an amount of from 30% by weight of the film to 55% by weight of the film.

* * * * *